United States Patent [19]

Juvinall

[11] 4,437,116

[45] Mar. 13, 1984

[54] METHOD AND APPARATUS FOR COMPARING DATA SIGNALS IN A CONTAINER INSPECTION DEVICE

[75] Inventor: John W. Juvinall, Ottawa Lake, Mich.

[73] Assignee: Owens-Illinois, Inc., Toledo, Ohio

[21] Appl. No.: 218,996

[22] Filed: Dec. 22, 1980

[51] Int. Cl.³ .............................................. H04N 7/18
[52] U.S. Cl. ................................................... 358/106
[58] Field of Search .............. 358/106, 107, 163, 280, 358/282; 356/430, 199, 200; 250/563

[56] References Cited

U.S. PATENT DOCUMENTS

| | | | |
|---|---|---|---|
| 3,379,826 | 4/1968 | Gray | 358/282 |
| 4,054,377 | 10/1977 | Gibson | 356/430 |
| 4,246,606 | 1/1981 | Yoshida | 358/106 |

*Primary Examiner*—Howard W. Britton
*Assistant Examiner*—Edward L. Coles
*Attorney, Agent, or Firm*—Gerald T. Welch; Myron E. Click

[57] ABSTRACT

The present invention relates to an apparatus and method for generating a comparison signal representing the magnitude difference between two successive video signals representing adjacent inspection points on the container. The comparison signal is generated with a magnitude representing the ratio between the two video signals. The ratio is calculated with the one of the two video signals having the larger magnitude as the denominator. A comparison signal generated in this manner is insensitive to general light variations across the container.

15 Claims, 3 Drawing Figures

METHOD AND APPARATUS FOR COMPARING DATA SIGNALS IN A CONTAINER INSPECTION DEVICE

CROSS-REFERENCE TO RELATED APPLICATION

The present invention is related to the sidewall inspection device described in U.S. patent application Ser. No. 205,054, filed Nov. 7, 1980, in the name of John W. V. Miller and entitled METHOD AND APPARATUS FOR RAPIDLY EXTRACTING SIGNIFICANT DATA FROM A SPARSE OBJECT, assigned to the assignee of the present application, and incorporated herein by reference.

BACKGROUND OF THE INVENTION

1. Field of the Invention

The present invention relates in general to sidewall inspection devices for containers and in particular to a method and apparatus for comparing individual video data signals from an inspection of a container, such as a glass bottle.

2. Description of the Prior Art

The use of optical scanning devices for inspecting the sidewalls of containers is well known. Numerous devices, such as those shown in U.S. Pat. Nos. 3,708,680 and 3,716,136, have circuitry including means for receiving and interpreting light passed through or directed onto an item under inspection. Such devices incorporate either a visual display for comparison of the item or employ a device capable of producing a resistance proportional to the intensity of light directed thereon. Whether the output of such a device is visual or electrical in nature, it is eventually compared against a model to determine if the item under inspection is suitable as to size and construction and is without flaws, cracks, or foreign objects. Such devices are each intended to provide an automated inspection means for checking, as in a moving column of bottles, single or multiple objects in that moving column.

U.S. Pat. No. 3,877,821 discloses an apparatus having a scanning array that is serially interrogated to generate a train of pulses having amplitudes representing the light transmitted through an object under inspection. Adjacent pulses are compared to generate pulses having amplitudes which represent the difference in pulse amplitudes. The difference pulses can be utilized to indicate a defect in the object being inspected. U.S. Pat. No. 3,942,001 discloses an apparatus for detecting the presence of extraneous matter or cracks in translucent containers. A beam of light is projected through the container to generate an inspection signal which is compared with an acceptance signal. The acceptance signal amplitude is varied in accordance with the position of the spot beam with respect to the container.

One of the problems associated with prior art inspection devices is the sensitivity of the inspection device to general light variations across the container. For example, in the above discussed U.S. Pat. No. 3,877,821, the amplitude of the difference pulse varies in accordance with the intensity of the light. Thus, if the intensity of light varies across the container, a difference pulse representing one type of defect in one portion of the container may be different in amplitude than a difference pulse representing a similar defect in another portion of the container subject to a different intensity of light.

SUMMARY OF THE INVENTION

The present invention is concerned with a method and apparatus for comparing video data signals generated from an inspection of a container in which the comparison is insensitive to general light variations across the container. A light source and camera are utilized to generate a series of video signals each having a magnitude corresponding to the amount of light received from a particular point of inspection, or pixel, on the container. Successive video signals represent adjacent pixels on the container.

A comparison circuit is responsive to the video signals for generating a comparison signal representing the magnitude difference between two successive video signals. In accordance with the present invention, the comparison signal is generated with a magnitude representing the ratio between the two successive video signals. The ratio is calculated with the one of the two successive video signals having the larger magnitude as the denominator. A storage means such as a sample-/hold circuit stores the first one of the two successive video signals until the second signal is generated.

In one embodiment of the invention, the comparator circuit utilizes a multiplying A/D converter to calculate the ratio between the two successive video signals which are supplied to inputs of the converter. A comparator senses the magnitudes of the two video signals and generates a signal to control a switch means such that the larger of the two signals is always supplied to the input of the A/D converter corresponding to the denominator of the ratio. This ratio is generated as the comparison signal.

In a second embodiment of the invention, the comparator circuit includes a pair of multiplying A/D converters which are used to calculate two separate ratios between the two successive video signals. The first ratio has a denominator corresponding to one of the two video signals and a numerator corresponding to the other signal, while the second ratio is the reciprocal of the first ratio. The one of the two ratios having a value less than one represents the ratio having the larger of the two video signals as the denominator. The comparator circuit includes means for selecting the one of the two ratios having a value less than one and for generating this ratio as the comparison signal.

Both embodiments can use a minimum detector which is connected to generate a minimum reference signal representing the minimum magnitude generated by one of the video signals during the inspection process. The minimum reference signal is used to offset the incoming video signals by the minimum magnitude. This enables the comparison circuit to use the full range of the A/D converters.

DESCRIPTION OF THE PREFERRED EMBODIMENTS

Figure 1:
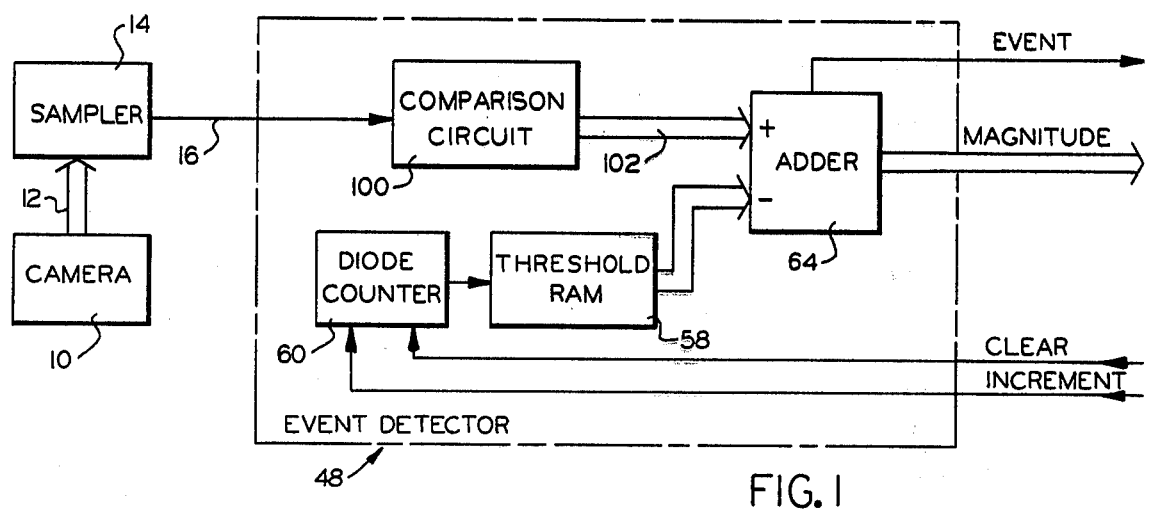
FIG. 1 is a block diagram of a portion of an inspection device to which the present invention is applicable.

Referring to FIG. 1, there is shown in block diagram form a portion of a sidewall inspection device for detecting defects in objects such as containers. Although FIG. 1 will be discussed briefly, a more detailed description of those elements shown in FIG. 1 and the remaining portion of the inspection device not shown in FIG. 1 can be found in the above-identified U.S. patent application entitled METHOD AND APPARATUS FOR RAPIDLY EXTRACTING SIGNIFICANT DATA FROM A SPARSE OBJECT, which is herein incorporated by reference. It should be noted that the reference numerals herein which are less than 100 correspond directly to elements which have been discussed in detail in the above-identified U.S. patent application.

In FIG. 1, an object, such as a glass bottle (not shown), is scanned by a camera 10. The camera 10 generates a plurality of signals proportional in magnitude to the amount of light received from the glass bottle. In the preferred embodiment of the invention, a light source (not shown) directs a beam of light through the glass bottle under inspection and into the camera 10. The camera 10 includes of a plurality of photosensitive devices, such as photodiodes, which are vertically arranged in a linear array. It has been found that a linear array of two hundred fifty-six photodiodes yields satisfactory results. A photodiode is a variable resistance device that will pass a voltage proportional to the amount of light falling thereon. Each photodiode receives light which has passed through a different inspection point of the bottle. An inspection point is typically referred to as a pixel. If a flaw, crack, or foreign object is contained in the bottle, then the light passing through the corresponding pixel of the bottle will be partially blocked or reflected and the corresponding photodiode will register a different intensity of light than had no defect been present.

The signals from the photodiodes of the camera 10 are supplied to a sampler 14 on a plurality of lines 12. Each of the photodiodes is sampled in a sequential order to produce a series of video pulse signals on a line 16 which represents the amount of light which has passed through the bottle under inspection along one vertical sequential check of the photodiodes. The sampler 14 is a device well known in the art. By rotating the bottle under inspection relative to the camera 10, a plurality of different sweeps can be made, each sweep inspecting a different portion of the bottle. It has been found that about three hundred seventy-five to four hundred different sweeps will sufficiently cover an average bottle and ensure an accurate inspection. Thus, the sampler 14 generates a plurality of video signals series on the line 16 each signal having a magnitude proportional to the amount of light passing through the respective point on the bottle.

The video signals generated by the sampler 14 on the line 16 are an input to an event detector 48 which represents a portion of the inspection device referred to as an inspection device interface (not shown in the drawings). The interface, which is discussed in detail in the above-identified incorporated reference, functions to rapidly extract significant data from the glass bottle in a manner which is suitable for computer analysis.

The event detector 48 includes a comparison circuit 100 which receives the video signals on the line 16 and generates a digital comparison signal on a line 102 to an adder 64. In the above-identified incorporated reference, the comparison circuit 100 comprises a latch 50, an adder 52, and an absolute magnitude circuit 56. These elements are not shown in the accompanying drawings, but are discussed in detail in the incorporated reference. The present invention is concerned with a comparison circuit which results in improved operation over the prior art comparison circuits. Basically, the comparison circuit 100 functions to generate a comparison signal on the line 102 representing the deviation between two successive video signals on the line 16.

The event detector 48 includes a threshold random access memory (RAM) 58 for storing a plurality of threshold signals. Each threshold signal stored in the RAM 58 corresponds to a specific comparison signal generated by the comparison circuit 100. A diode counter 60 is utilized to select the individual threshold signal from the RAM 58 which corresponds to the present comparison signal generated by the circuit 100. The diode counter 60 can be reset to zero by a CLEAR signal and can be incremented by an INCREMENT signal. Both the CLEAR signal and the INCREMENT signal can be generated by a control logic unit 54 (not shown) of the interface 18.

The signal from the threshold RAM 58 is supplied to a complementary input of an adder 64 where it is combined with the comparison signal on the line 102. When the magnitude of the comparison signal on the line 102 exceeds the magnitude of the corresponding threshold signal, the adder 64 generates an EVENT signal to inform the interface 18 that the detector 48 has detected a defect. The adder 64 can also generate a MAGNITUDE signal to inform the interface 18 as to the difference in magnitude between the comparison signal on the line 102 and the corresponding threshold signal.

Figure 2:
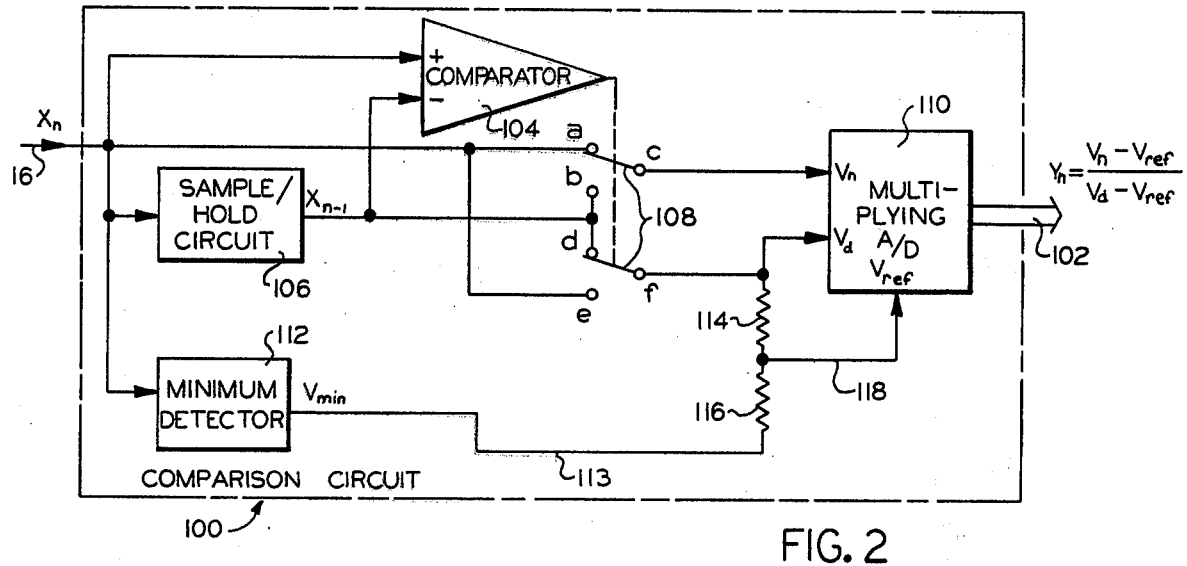
FIG. 2 is a block diagram of one embodiment of the comparison circuit of FIG. 1 according to the present invention.

There is shown in FIG. 2 a block diagram of one embodiment of the comparison circuit 100 according to the present invention. Basically, the comparison circuit according to the present invention functions to generate a comparison signal on the line 102 which is representative of the magnitude difference between two successive video signals generated on the line 16. As will be discussed, the method according to the present invention results in a comparison signal which is insensitive to ambient light variations across the bottle.

In FIG. 2, the video signal $X_n$ on the line 16 is supplied to a (+) input of a comparator 104 and the input of a sample/ hold circuit 106. The signal $X_n$ represents the light received from the presently sampled pixel. The signal $X_n$ is also supplied to terminals (a) and (e) of a double pole, double throw switch 108 which is connected to be controlled by the output of the comparator 104.

The sample/hold circuit 106 functions to store the $X_n$ signal until the next successive video signal is generated on the line 16. At this time, the value stored in the circuit 106 will be $X_{n-1}$, where $X_{n-1}$ represents the light received from the preceeding pixel. The $X_{n-1}$ signal is supplied to the (−) input of the comparator 104 and to terminals (b) and (d) of the switch 108. The switch 108 has a terminal (c) connected to a $V_n$ input and a terminal (f) connected to a $V_d$ input of a multiplying analog-to-digital (A/D) converter 110. The A/D converter 110 is connected to generate the comparison signal on the line 102.

The comparison circuit 100 of FIG. 2 also includes a minimum detector 112 connected to receive the video signals on the line 16. The detector 112 senses the magnitudes of the incoming video signals on the line 16 and generates a $V_{min}$ signal on a line 113 representing the minimum magnitude sensed during the inspection process. A voltage divider comprising a pair of resistors 114 and 116 is connected between the $V_d$ input of the converter 110 and the line 113. A line 118 supplies the voltage present at the junction of the resistors 114 and 116 to a $V_{ref}$ input of the A/D converter 110.

In operation, the comparator 104 functions to sense the magnitudes of the $X_n$ signal and the $X_{n-1}$ signal and control the switch 108 such that the signal having the larger magnitude is always supplied to the Vd input of the multiplying A/D converter 110. The converter 110 will then calculate the comparison signal $Y_n$ based on the magnitudes present at the inputs $V_n$, $V_d$, and $V_{ref}$ in accordance with the following equation: $Y_n = (V_n - V_{ref})/(V_d - V_{ref})$. As will be discussed, this equation results in a comparison signal $Y_n$ which is insensitive to the light level common to both $X_n$ and $X_{n-1}$ and is therefore insensitive to gradual illumination differences.

The magnitude of the signal at the input $V_{ref}$ represents the offset which is combined with the signals at the $V_n$ and $V_d$ inputs before the comparison ratio is calculated. As previously mentioned, the signal $V_{min}$ on the line 113 represents the minimum magnitude of the $X_n$ video signals on the line. This minimum magnitude is typically referred to as the dark signal level. If the $V_{min}$ signal is supplied directly to the $V_{ref}$ input of the converter 110, the converter 110 will generate a comparison signal on the lines 102 which has been corrected for the dark signal level offset. This enables the comparison circuit 100 to utilize the entire range of the A/D converter 110 in calculating the comparison signal.

The accuracy of the comparison of small pixel to pixel variations can be increased by utilizing the voltage divider in FIG. 2 to increase the magnitude of the $V_{min}$ signal before it is supplied to the $V_{ref}$ input. For example, if the values of the resistors 114 and 116 were equal, the voltage supplied to the $V_{ref}$ input would be $V_{ref} = V_{min} + (V_d - V_{min})/2$. In this case, a pixel to pixel variation of 50% or less will utilize the full range of the A/D converter, while variations greater than 50% will always result in a comparison signal of zero. This method of increasing the magnitude of the $V_{min}$ signal before supplying it to the $V_{ref}$ input is especially desirious where the range of the A/D converter 110 is limited and/or the normal pixel to pixel variations are not expected to be large.

In comparing the prior art method of pixel differencing to the method according to the present invention, the advantages of the present invention can be readily seen. In the prior art method of pixel differencing, the comparison signal $Y_n$ was calculated as follows $Y_n = X_n - X_{n-1}$. Thus, if $X_n$ had a magnitude of four and $X_{n-1}$ had a magnitude of three, the comparison signal $Y_n$ would equal one for a given amount of illumination. However, if the illumination were increased twofold, the prior art method of comparison would result in a comparison signal having a value of two. Thus, in the prior art method of pixel differencing, the ambient light across the bottle had to remain relatively uniform such that similar responses were obtained for similar defects. The present invention permits a gradual illumination variation across the bottle without affecting the value of the comparison signal. For example, in the method of the present invention, assuming an offset of zero, if the signals to inputs $V_d$ and $V_n$ were equal to four and three respectively, the comparison signal $Y_n$ would equal $\frac{3}{4}$. If the illumination were increased such that for the same defect $V_d$ had a value of eight and $V_n$ had a value of six, the comparison signal $Y_n$ would still equal $\frac{3}{4}$. Thus, the present method results in the same comparison signal for the same defect, regardless of the ambient light level common to both $X_n$ and $X_{n-1}$.

Figure 3:
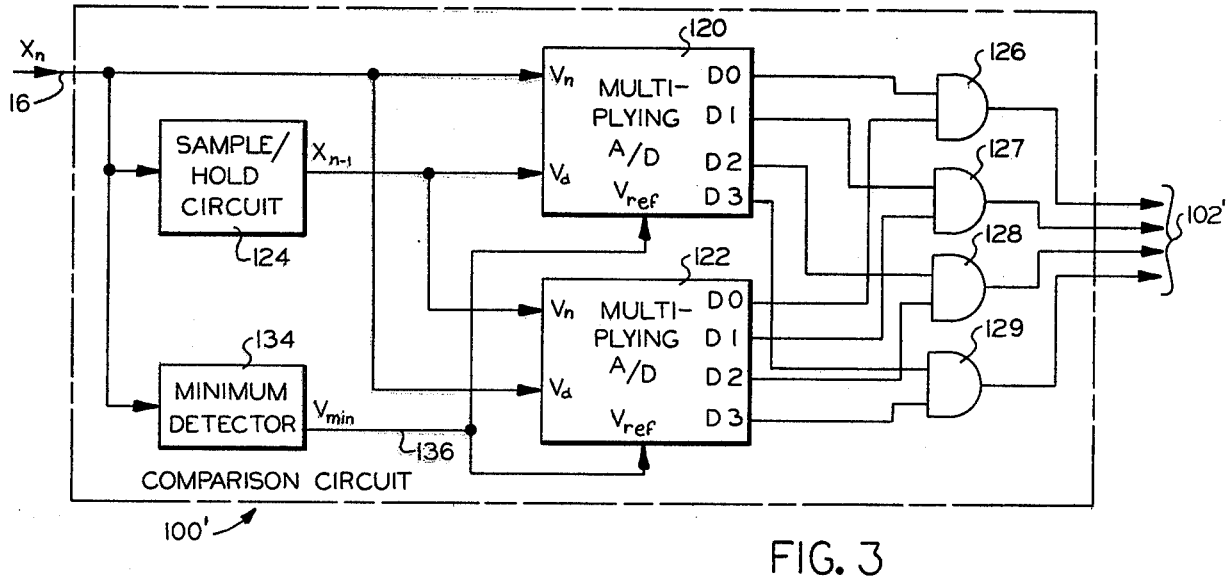
FIG. 3 is a block diagram of an alternate embodiment of the comparison circuit of FIG. 1 according to the present invention.

There is shown in FIG. 3 an alternate embodiment 100' of a comparison circuit according to the present invention. The video signal on the line 16 is supplied to a $V_n$ input of a multiplying A/D converter 120 and to a $V_d$ input of another multiplying A/D converter 122. The video signal is also supplied to a sample/hold circuit 124 which functions to store and generate the preceding pixel signal $X_{n-1}$. The $X_{n-1}$ signal is supplied to a $V_d$ input and a $V_n$ input of the A/D converters 120 and 122 respectively. The A/D converters 120 and 122 each function to calculate a ratio based on the incoming analog signals and generate a four bit digital output signal at the four output terminals D0 through D3.

The output terminals D0–D3 of the A/D converter 120 are each connected to one input of a group of four AND gates 126 through 129 respectively. Similarly, the output terminals D0–D3 of the A/D converter 122 are each connected to the other input of the AND gates 126 through 129 respectively. The outputs of the AND gates are combined to generate the comparison signal on the lines 102'. It should be noted that although four bit A/D converters are shown in FIG. 3, A/D converters having a larger number of output terminals can also be used. In this case, additional AND gates would be provided such that the number of AND gates corresponded to the number of output terminals in each A/D converter.

As was the case for the circuit FIG. 2, the comparison circuit 100' also includes a minimum detector 134 connected to receive the video signals on the line 16 and generate a $V_{min}$ signal on a line 136. The detector 134 functions in a manner similar to the detector 112 of FIG. 2. In FIG. 3, the $V_{min}$ signal on the line 136 is supplied to the $V_{ref}$ inputs of both the A/D converters 120 and 122 where it is subtracted from the $V_n$ and $V_d$ signals before the ratios are calculated. If desired, a voltage divider (not shown) can be utilized in a manner similar to the voltage divider of FIG. 2 to increase the magnitude of the $V_{min}$ signal before it is supplied to the $V_{ref}$ inputs.

In operation, the circuit of FIG. 3 functions to calculate two separate ratios. The A/D converter 120 will calculate a first ratio having the $X_n$ signal in the numerator and the $X_{n-1}$ signal in the denominator. The A/D converter 122 will calculate a second ratio having the $X_{n-1}$ signal in the numerator and the $X_n$ signal in the denominator. Both A/D converters are set such that when the calculated ratio is one or greater, all the outputs of the respective converter will be at logic "1." In every case, the ratio calculated by one of the A/D converters will be one or greater, while the ratio calculated by the other A/D converter will be one or less than one. The ratio which is less than one represents the ratio wherein the one of the $X_n$ and $X_{n-1}$ signals having the larger magnitude is in the denominator. The A/D converter having all logic "1" outputs will enable the AND gates 126 and 129 such that the output of the other A/D converter will be generated on the lines 102 as the comparison signal.

It should be noted that the present invention in its broadest sense encompasses the idea of dividing one video pixel signal by a second video pixel signal to generate a comparison signal which represents the ratio of the two signals. However, from a practical standpoint, it is generally not desirious to have a ratio which can cover a wide range of values. This is especially true where a limited range A/D converter is used to convert an analog signal into digital form. For example, such a ratio may result in relatively large values if the denominator is significantly smaller than the numerator. Accordingly, the comparison circuit of the present invention includes means for calculating the ratio with the larger of the two video signals in the denominator, thus ensuring that the ratio will be equal to or less than one. This makes the present invention readily adaptable to computer-controlled digital circuits.

It should also be noted that there are other methods available for incorporating the minimum detector into the comparison circuits of FIG. 2 and FIG. 3. For example, the $V_{min}$ signal could be subtracted from the incoming video signals $X_n$ on the line 16.

In accordance with the provisions of the patent statutes, the principle and mode of operation of the invention has been explained and illustrated in its preferred embodiment. However, it must be understood that the invention may be practiced otherwise than as specifically illustrated and described without departing from the spirit or scope.

What is claimed is:

1. In an apparatus for detecting defects in an object including a camera for generating a series of video signals each having a magnitude proportional to an amount of light received from a particular point of inspection on the object, a circuit for generating a comparison signal representing a magnitude difference between two of the video signals, said circuit comprising; means responsive to the two video signals for generating a comparison signal having a magnitude representing a ratio of the one of the two video signals having the smaller magnitude to the other one of the two video signals having the larger magnitude.

2. The circuit according to claim 1 including means for storing the first one of the two video signals.

3. The circuit according to claim 1 wherein said means for generating said comparison signal includes a multiplying analog-to-digital converter having a first input connected to receive the one of the two video signals having the smaller magnitude and a second input connected to receive the other one of the two video signals, said converter calculating said ratio by dividing the video signal present at said first input by the video signal present at said second input.

4. The circuit according to claim 3 wherein said means for generating said comparison signal includes a switch means for connecting each one of the two video signals to the corresponding input of said converter.

5. The circuit according to claim 4 wherein said means for generating said comparison signal includes a comparator responsive to the magnitudes of the two video signals for generating an output signal to control said switch means.

6. In an apparatus for detecting defects in an object including a camera for generating a series of video signals each having a magnitude proportional to an amount of light received from a particular point of inspection on the object, a circuit for generating a comparison signal representing a magnitude difference between two of the video signals, said circuit comprising: means responsive to the two video signals for generating a comparison signal having a magnitude representing a ratio between the two video signals and minimum detector means responsive to said series of video signals for generating a minimum reference signal representing the minimum magnitude of the series of video signals.

7. The circuit according to claim 6 including means responsive to said minimum reference signal for offsetting the incoming video signals by said minimum magnitude.

8. In an apparatus for detecting defects in an object including a camera for generating a series of video signals each having a magnitude proportional to an amount of light received from a particular point of inspection on the object, a circuit for generating a comparison signal representing a magnitude difference between two of the video signals, said circuit comprising: means responsive to the two video signals for generating a comparison signal having a magnitude representing a ratio between the two video signals, said generating means including a first multiplying means for determining a first ratio having one of the two video signals as a numerator and the other one of the video signals as a denominator; a second multiplying means for determining a second ratio having the other one of the video signals as a numerator and the one of the video signals as a denominator; and means for selecting the one of said first and second ratios having a value equal to or less than one and generating said selected ratio as said comparison signal.

9. The circuit according to claim 8 wherein said first and second multiplying means are multiplying analog-to-digital converters for generating said respective ratios in digital form and said means for selecting are a plurality of AND gates each having one input connected to receive said first ratio and another input connected to receive said second ratio such that the comparison signal is generated at outputs of said AND gates.

10. A method of generating a comparison signal representing a magnitude difference between two video signals generated by an apparatus for detecting defects in an object including a camera for generating a series of video signals each having a magnitude proportional to an amount of light received from a particular point of inspection on the object, the method comprising the steps of:
   (a) generating a first ratio signal having one of the two video signals as a numerator and the other one of the two video signals as a denominator and a second ratio signal having the other one of the two signals as a numerator and the one of the two signals as a denominator; and
   (b) generating the comparison signal having a magnitude representing the one of the first and second ratio signals which is equal to or less than one.

11. The method according to claim 10 including the step of storing the first one of the two video signals prior to step (a).

12. The method according to claim 10 including the step of offsetting the two video signals by a minimum reference signal representing the minimum of the magnitude of the series of video signals.

13. A method for generating a comparison signal representing a magnitude difference between two video signals generated by an apparatus for detecting defects in an object including a camera for generating a series of video signals each having a magnitude proportional to an amount of light received from a particular point of inspection on the object, the method comprising the steps of:
(a) determining a first ratio having one of the video signals as a numerator and the other one of the signals as a denominator;
(b) determining a second ratio having the other one of the video signals as a numerator and the one of the signals as a denominator;
(c) selecting the one of the first and second ratios having a value less than one; and
(d) generating the comparison signal having a magnitude equal to the selected one ratio.

14. The method according to claim 13 including the step of storing the first one of the two video signals prior to step (a).

15. The method according to claim 13 including the step of offsetting the two video signals by a minimum reference signal representing the minimum of the magnitudes of the series of video signals.

* * * * *